United States Patent [19]
Hoffman et al.

[11] Patent Number: 5,188,098
[45] Date of Patent: Feb. 23, 1993

[54] METHOD AND APPARATUS FOR ECG GATED VENTILATION

[75] Inventors: Eric A. Hoffman, Narberth; C. William Hanson, III, Philadelphia, both of Pa.

[73] Assignee: The Trustees of the University of Pennsylvania, Philadelphia, Pa.

[21] Appl. No.: 787,635

[22] Filed: Nov. 4, 1991

[51] Int. Cl.$^5$ ............................................ A61M 16/00
[52] U.S. Cl. ................................................ 128/204.23
[58] Field of Search ...................... 128/204.23, 204.18, 128/204.21, 205.23

[56] References Cited

U.S. PATENT DOCUMENTS

| | | | |
|---|---|---|---|
| 4,461,293 | 7/1984 | Chen | 128/204.23 |
| 4,519,387 | 5/1985 | Durkan et al. | 128/204.23 |
| 4,535,766 | 8/1985 | Baum | 128/204.23 |
| 4,982,735 | 1/1991 | Yagata et al. | 128/204.23 |
| 5,005,570 | 4/1991 | Perkins | 128/204.23 |
| 5,016,626 | 5/1991 | Jones | 128/204.23 X |
| 5,044,362 | 9/1991 | Younes | 128/204.21 |
| 5,107,831 | 4/1992 | Halpern et al. | 128/204.23 X |
| 5,129,390 | 7/1992 | Chopin et al. | 128/204.21 |

OTHER PUBLICATIONS

M. R. Pinsky, et al., "Determinants of Cardiac Augumentation By Elevations In Intrathoracic Pressure", Journal of Applied Physiology, vol. 58(4) pp. 1189-1198 (1985).

M. R. Pinsky, et al., "Hemodynamic Effects Of Cardiac Cycle-Specific Increases In Intrathoracic Pressure", Journal of Applied Physiology, vol. 60(2) pp. 604-612 (1986).

Primary Examiner—William H. Grieb
Attorney, Agent, or Firm—Woodcock Washburn Kurtz Mackiewicz & Norris

[57] ABSTRACT

Method and apparatus for maximizing the volume of blood pumped by a heart and maximizing ventilation/-perfusion matching in the lungs, wherein the lungs are ventilated by a respirator in response to a control signal, are shown to include a series of monitors for generating a heart signal such as an electrocardiogram, a lung air flow rate signal and a lung air pressure signal and a controller, connected to receive these signals and to the respirator. The controller monitors the signals and generates the control signal when the heart signal is representative of a desired in point in the pumping cycle of the heart and the other signals indicate desired flow rate and pressure in the lungs. In a preferred embodiment, the control signal is generated so as to maximize the augmentation of the pumping of the heart and to minimize the trapping of air in the lungs. Using the present invention, blood being pumped from the heart is assisted by the ventilation of the lungs. It is preferred for the controller to include a series of threshold detectors for detecting when the signals exceed threshold levels. It is especially preferred for the detector to detect a point during ventricular contraction. It is especially preferred for the apparatus to further include a delay mechanism, interposed between the respirator and the controller, for delaying the control signal.

16 Claims, 3 Drawing Sheets

METHOD AND APPARATUS FOR ECG GATED VENTILATION

The research disclosed in this patent application was supported in part by National Institutes of Health. The United States government has certain rights in the invention.

FIELD OF THE INVENTION

The present invention relates generally to the field of cardio-pulmonary physiology and particularly to methods and apparatus for augmenting cardiac output.

BACKGROUND OF THE INVENTION

A recurrent problem in the medical and surgical intensive care field is the patient with coextensive respiratory and cardiac failure. Patients exhibiting this condition are typically treated through the use of positive pressure ventilation techniques, such as standard volume cycled ventilation, inotropic infusions and not infrequently with mechanical cardiac assist devices such as the intra-aortic balloon pump (IABP) or the ventricular assist device (VAD).

It will be appreciated that inotropic infusions have inherent risks and benefits. While they may improve perfusion, i.e. the movement of fluids, through cardiac and cerebral circulation systems, there may be detrimental effects to perfusion in pulmonary and splanchnic circulation systems.

Unfortunately, devices such as the IABP or VAD necessitate intravascular placement of a foreign body, i.e. surgical implantation, with the attendant risk of infection or vascular injury. Additionally, IABP provides cardiac assistance based on the principal of cardiac cycle-specific changes in the volume and pressure of the proximal aorta through the use of an intra-aortic balloon. When implementing IABP, cardiac afterload is decreased during systole, i.e. ejection of fluid from the heart, by deflating the balloon. Cardiac afterload is that parameter indicative of volume and pressure of the proximal aorta. Deflation of the balloon enhances so-called stroke volume—forward blood flow. Cardiac afterload is increased during diastole, i.e. filling of the heart, by inflating the balloon, thereby enhancing coronary perfusion.

In the present invention, cardiac cycle-specific non-invasive changes in intra-thoracic pressure are used to effectuate changes on ventricular preload and afterload and by direct mechanical action on the myocardium to improve cardiac performance. Studies relating to changes in intrathoracic pressure have been carried out. See M. R. Pinsky et al., Determinants of cardiac augmentation by elevations in intrathoracic pressure, Journal of Applied Physiology, Vol. 58 (4), pps. 1189–1198 (1985) and M. R. Pinsky et al., Hemodynamic effects of cardiac cycle-specific increases in intrathoracic pressure, Journal of Applied Physiology, Vol. 60 (2), pps. 604–612 (1986). However, such studies on laboratory specimens, particularly mongrel dogs, have found that absent the use of constrictive devices such as thoracoabdominal binding, inspiratory jet pulses from a high frequency jet ventilator had minimal hemodynamic effects as evidenced by small changes in pleural pressure. Furthermore, the authors were only able to demonstrate an effect on the failing heart, not on the normally functioning heart. One of the problems associated with these studies is that the thorax of the subject specimens had to be opened and several monitoring devices implanted. Furthermore, these studies concentrated only on the effect of cardiac gated respiration on the heart. It did not evaluate the effect of this modality on ventilation/perfusion relationships in the lungs.

Unfortunately, the unique interactions between the heart and lungs in the negative-pressure environment of the intact thorax have been difficult to study quantitatively. Consequently, these unique interactions have been studied only on a limited basis via non-invasive techniques. Developments in recent years to three-dimensional imaging have gone a long way toward providing satisfactory techniques to non-invasively assess intrathoracic organ geometry and function.

An ultra-fast X-ray computed tomography (CT) scanner has been produced by Imatron Corporation which is capable of acquiring two (2) slices of the body every 50 ms. By combining such a CT scanner together with equipment to focus the scanner on particular physiologic conditions, non-invasive data relating to precise physiologic conditions can be gathered. When such data is interrogated utilizing new software packages, post analysis of the 4-dimensional data sets can be achieved. One such package is the VIDA ™ imaging software developed at the Cardiac Imaging Research Center, Department of Radiology at the Hospital of the University of Pennsylvania. Utilizing such equipment, non-invasive studies of the thorax are possible which may prove beneficial to patients experiencing either cardiac failure alone, respiratory failure alone or a combination of cardiac and respiratory failure.

A need exists for apparatus and/or methods for treating cardiac and/or respiratory failure which apparatus and methods are non-invasive in relation to the thorax, whereby cardiac and/or respiratory function are not diminished in the process of augmenting one system or the other.

SUMMARY OF THE INVENTION

The advantages of the invention are achieved in a method and apparatus for maximizing the volume of blood pumped by a heart, wherein the lungs are ventilated by a respirator in response to a control signal. The invention is shown to include a series of monitors for generating a heart signal such as an electrocardiogram, a lung air flow rate signal and a lung pressure signal and a controller, connected to receive the signals and to the respirator. The controller monitors the signals and generates the control signal when the heart signal is representative of a desired point in the pumping cycle of the heart and when the lungs exhibit desired air flow rate and pressure. This achieves maximum enhancement of cardiac output and avoids air trapping in the lungs.

Experiments using non-invasive measuring techniques, have demonstrated that respiratory gating in early diastole puts expiration during systole. For the first time, it has been demonstrated that airway restrictions occur during systole, and thus expiration occurring during systole, is impeded. Furthermore, the distribution of pulmonary blood flow throughout the lung is altered variably depending upon the phase relationship between the respiratory and cardiac cycle.

Using the present invention, blood being pumped from the heart is assisted by the ventilation of the lungs. It is preferred for the controller to include a series of threshold detectors for detecting when the heart, flow rate and pressure signals exceed threshold levels. It is especially preferred for the detector to detect a point during ventricular contraction. It is also preferred for each detector to include a comparator and a variable reference signal generator, whereby the comparator compares the received signal to a signal generated by a variable reference signal generator. It is especially preferred for the apparatus to further include a delay mechanism, interposed between the respirator and the controller, for delaying the control signal.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which.

DETAILED DESCRIPTION OF THE PREFERRED EMBODIMENT

Figure 1:
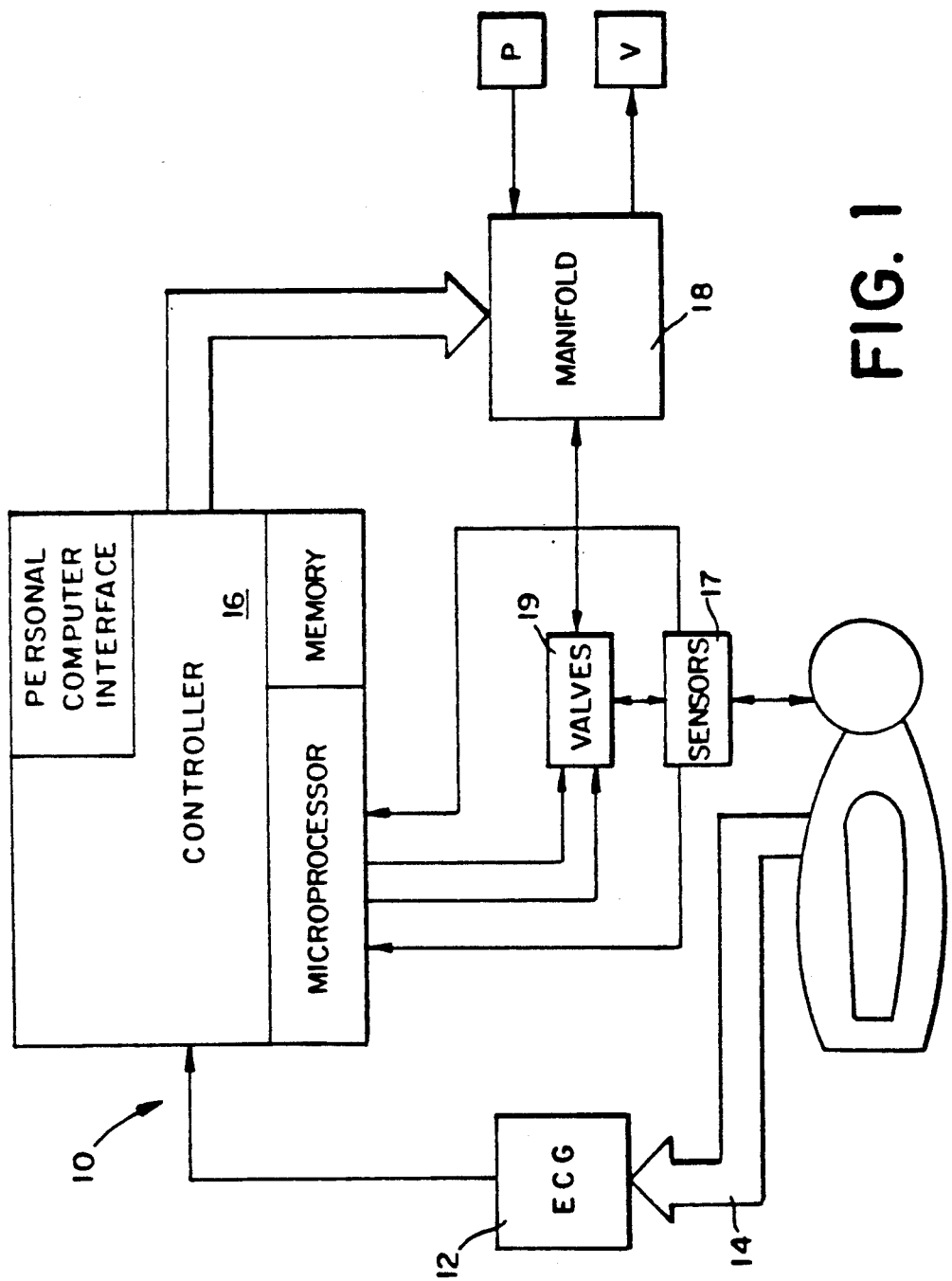
FIG. 1 is a diagrammatic view of a cardiac augmentation device constructed in accordance with the principles of the present invention.

A new and novel cardiac augmentation device is shown in FIG. 1 and generally designated 10.

Device 10 is shown to include an ECG monitor 12 for generating a heart signal representative of heart action. As will be appreciated, monitor 12 includes a plurality of leads 14 which are connected at various known locations to a patient. The electrical signals provided on such leads are utilized in a known manner to produce an electrocardiogram signal. The heart or electrocardiogram signal is provided to controller 16. Signals representative of the air flow rate into the lungs and the pressure of air flowing into or out of the lungs are generated by sensors 17. Sensors 17 can include any known devices for generating electrical signals representative of flow rate and pressure conditions.

It is noted that the present invention is described in relation to the use of an endotracheal tube (not shown) inserted in the patient. In operation, sensors 17 would be attached to such a tube in order to monitor pressure and flow rate during inspiration and expiration.

Controller 16 monitors the heart signal, the flow rate signal and the pressure signal and generates a control signal in response to the heart signal being representative of a desired point in the pumping cycle and the flow rate and pressure are at desired levels. The control signal is provided to manifold 18. In the preferred embodiment the control signal is representative of a calculated or programed desired air pressure for either inspiration or expiration. Such calculations and programming will be described more fully hereinafter. It is preferred for controller 16 to incorporate a computer printed circuit board based on the Hitachi 64180 microprocessor.

Manifold 18 is connected to a source of pressurized air P and to a vacuum source As will be more fully described, manifold 18 will switch between pressure and vacuum sources depending on whether controller 16 is controlling inspiration or expiration. The output of manifold 18 is also connected to valves 19. As will be described in relation to FIG. 3, valves 19 are operative to permit expiration without passing such expired air through manifold 18, i.e. permit expiration without a vacuum assist.

It will be appreciated that controller 16 and manifold 18 constitute the primary components of a respirator, which in the preferred embodiment is of the type designed for attachment to an endotracheal tube. The present invention can be practiced with any known and available respirator design which causes ventilation of the lungs in response to a control or an enabling signal. By applying an enabling signal to a respirator, the respirator is caused to be operative, i.e., to begin inspiration, upon receipt of the enabling signal. It has been found that by gating the respirator, i.e. controlling manifold 1B, to a particular point in the pumping cycle and to flow rate and pressure conditions, blood pumped from the heart is assisted by ventilation of the lungs.

It is noted that the flow rate and pressure signals generated by sensors 17 at the endotracheal tube site may also be generated by respirator 18 in relation to air flow rates and pressures applied to the patient. The generation of such signals in the respirator would provide an open loop control system rather than the closed loop system depicted in FIG. 1.

In the preferred embodiment, controller 16 and manifold 18 are the primary components of a CTP-9000 programmable ventilator system manufactured and sold by CWE Inc. of Ardmore, Pa. Although such ventilator is preferred, any ventilator wherein inspiration can be initiated by means of an enabling or control signal with high frequency response can be utilized. It is especially preferred for the chosen respirator to have the capability of programmable respiratory cycles and to exhibit quick response to programmed variation of respiratory parameters. In the preferred embodiment, controller 16 can be hosted by a master controller, preferably a personal computer for communicating pressure and vacuum profiles to the microprocessor.

Consequently, the flow rate and pressure of air inspired to and expired from the lungs can be controlled from a personal computer having a serial port. Using such a system, one can program respirator 18 for the present invention by setting flow rate, pressure, inspiration time and expiration time. Upon receipt of the control signal, the programmable respirator will initiate inspiration. In such a system, it is possible and preferred to designate certain function keys on a personal computer to effectuate changes in flow rate or inspiration time. It is also preferred to program respirator 18 to cause inspiration for a fixed time period or to cause inspiration to reach a desired pressure level.

Figure 2:
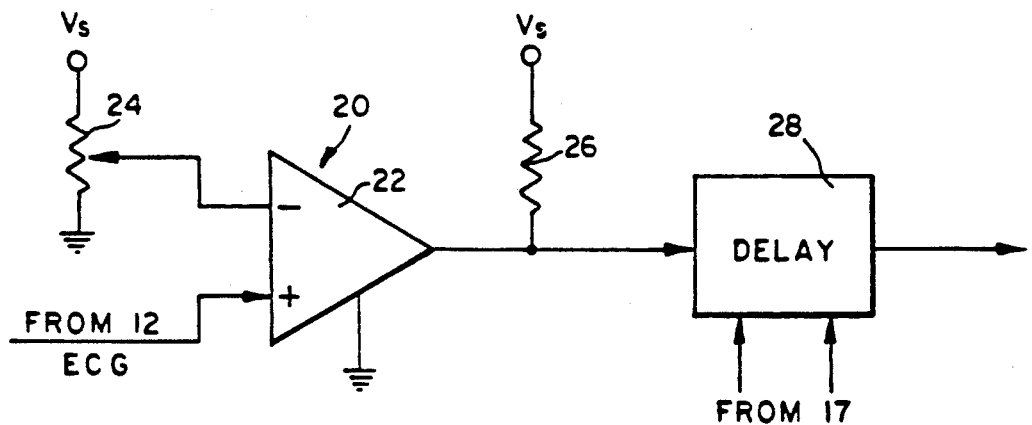
FIG. 2 is a more detailed diagram of the ECG gating portion of the invention shown in FIG. 1.

It will be understood that the ECG signal generated by monitor 12 includes a QRS portion. A distinct voltage peak is present in this portion. By sensing the voltage of the ECG signal, it is possible to detect the QRS peak and thereby synchronize the generation of a control or enabling signal in relation to the detection of the peak. To this end, one embodiment of the invention envisions the usage of threshold detector 20 as shown in FIG. 2.

Detector 20 is depicted as including an operational amplifier, arranged as a comparator, having its negative input connected to a reference voltage and its positive input connected to receive the ECG signal from monitor 12. The reference signal is generated by the connection of variable resistor 24 between a supply voltage $V_s$ and ground. It is noted that as the ECG voltage approaches the reference voltage, the output of operational amplifier 22 will change from a logic high to a logic low. The logic high output of operational amplifier 22 is provided by resistor 26 connected to supply voltage $V_s$. When ECG voltage is less than the reference voltage, current passing through 26 is directed to ground through operational amplifier 22. When ECG voltage exceeds the reference voltage, the current passing through resistor 26 is applied to delay circuit 28. In other words, the input to delay circuit 28 alternates between a logic high and logic low level depending on the voltage of the ECG signal.

In the preferred embodiment, delay circuit 28 is of any known design capable of providing a time delay. Delay circuit 28 also includes circuitry for indicating flow rate and pressure. Such circuitry can include threshold detectors identical to detector 20, wherein the reference voltage is selected to detect a given level of pressure or flow rate. It is especially preferred that such time delay be variable. If multiple detectors are included, such time delay can be event based, i.e. the control signal would be delayed until each detector detects desired conditions. In such a situation, the outputs of the detectors could be provided as inputs to an AND gate. If the flow rate and pressure detectors are constructed to provide visual indications of flow rate and pressure to an operator, delay circuit 28 would be constructed to provide a variable timing control, e.g. a variable resistor connected with a capacitor to provide a variable time constant circuit.

By providing a variable delay, one can make whatever fine adjustments are necessary in order to ensure that the enabling signal provided by respirator 18 initiates inspiration sa as to enhance cardiac output. It will be appreciated that there may be some delay in respirator 18 processing the enabling signal and initiating the inspiration cycle. A variable delay could be adjusted to account for such respirator delay.

Figure 3:
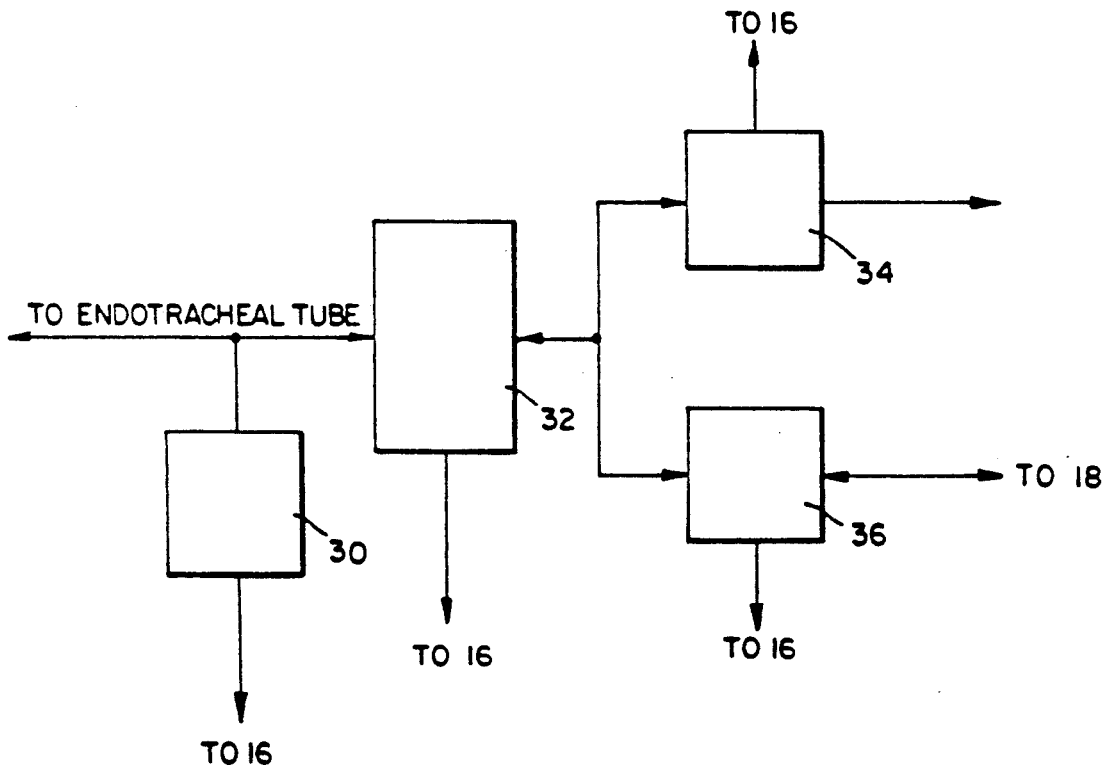
FIG. 3 is a more detailed diagram of the valves and sensors shown in FIG. 1.
Figure 4:
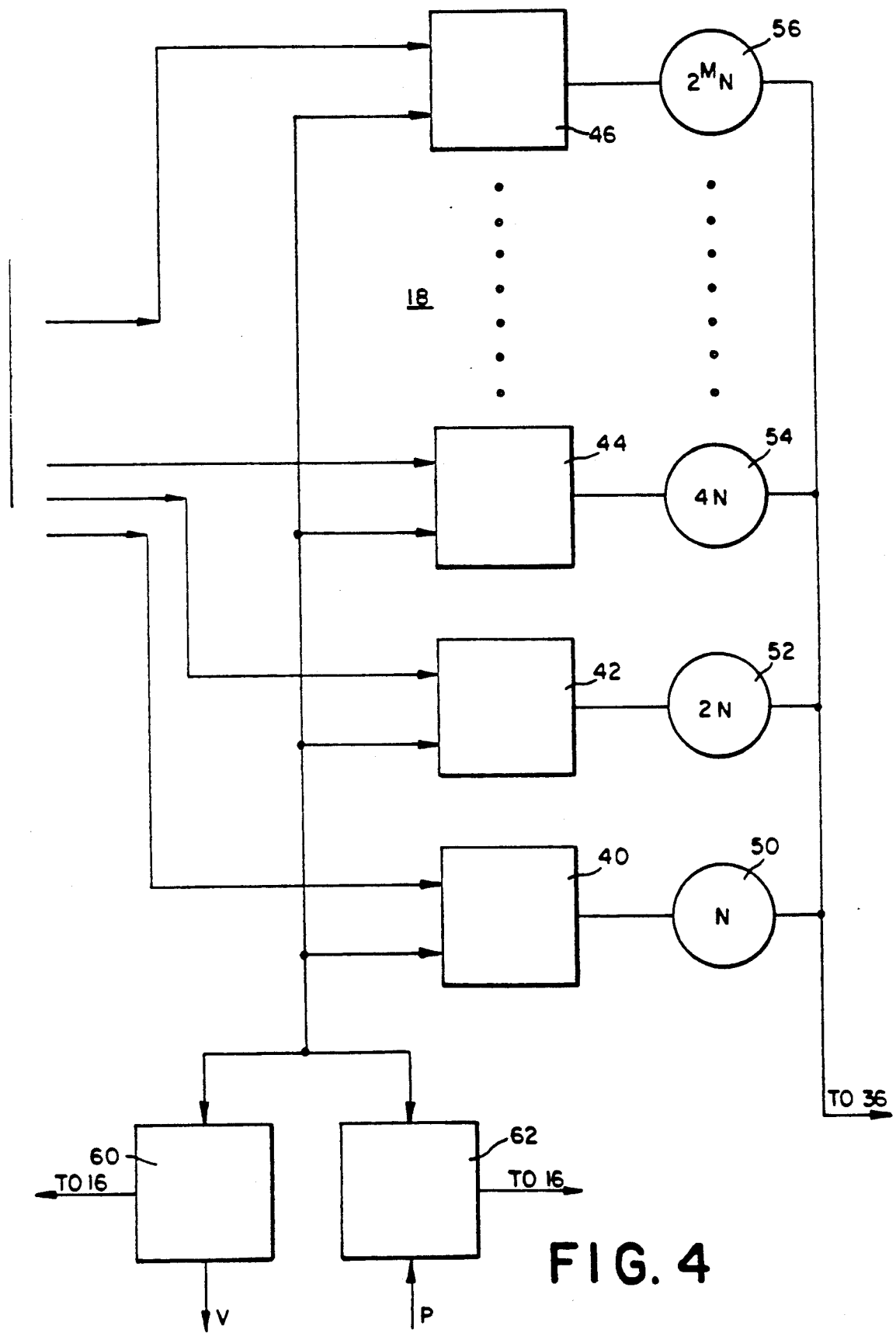
FIG. 4 is a more detailed diagram of the manifold shown in FIG. 1.

Referring now to FIG. 3, sensors 17 and valves 19 will be described in greater detail. Pressure transducer 30 is connected to the line connecting flow transducer 32 and the endotracheal tube previously mentioned. Transducer 30 generates an electrical signal representative of the air pressure present in the endotracheal tube and thus in the lungs. Similarly, transducer 32 generates an electrical signal representative of the flow rate of fluid passing to or from the endotracheal tube. Transducers 30 and 32 can be any transducer which will provide an electrical signal of pressure and flow, respectively. Such electrical signals are provided to controller 16. Valves 34 and 36 are provided so that expiration and possibly inspiration can occur without the vacuum or pressure assist provided via manifold 18. As will be appreciated, if valve 34 is closed and valve 36 is open, inspiration and expiration will occur via manifold 18. If valve 36 is closed and valve 34 is open, expiration and inspiration can occur without the assist provided via manifold 18. Although no particular valve is required for purposes of the invention, it is preferred to utilize valves which are electrically actuatable. As shown in FIG. 3, valves 34 and 36 are actuatable in response to signals from controller 16.

In the CTP-9000 the capability to program respiratory cycles is achieved through the use of a series of solenoid valves 40, 42, 44 and 46 and needle valves 50, 52, 54 and 56. The actuation signal used to control the solenoid valves is computer generated. It will be appreciated that the solenoid valves require a digital type signal, i.e. ON or OFF. Such a signal is generated by controller 16 generating a digital word which is M bits in length. The word is preferably stored in an M bit latch (not shown) while in use. The signal associated with each bit is provided to a different solenoid valve. The state of each valve, i.e. opened or closed, will depend on the value of the bit provided a given valve. In the preferred embodiment M is equal to 8.

Needle valves 50–56 are pre-set such that only a portion of the pressure or vacuum value is permitted to act therethrough. In the preferred embodiment each needle valve is pre-set to permit flow rate or vacuum equal to a multiple of N, where N equals 0.1 liters/minute. Accordingly, if the digital word provided by controller 16 to the solenoid valves is 00000001, only 0.1 liters/minute of either vacuum or pressure will act through manifold 18. By utilizing multiples of N, manifold 18 can permit any pressure or vacuum value to be applied to a patient in 0.1 liters/minute steps, by manipulating the ON/OFF state of the solenoid valves.

Valves 60 and 62 serve to control whether pressure or vacuum is applied to the solenoid valves and thereby to the patient. Valves 60 and 62 are also solenoid type valves responsive to an ON/OFF type signal. As shown in FIG. 3, such signals are provided by controller 16.

From the above, it wi-11 be appreciated that controller 16 can control both inspiration and expiration of the patient in steps as small as 0.1 liters/minute. Accordingly, the intricacy of a pressure or vacuum profile is limited by only the ability to generate digital words, for bit wise provision to solenoid valves 40–46 and by the response time associated with the particular solenoid valves used.

It is particularly preferred to initiate inspiration at the beginning of the contraction of the left ventricle. Since such contraction can be determined from the electrocardiogram signal, it is preferred that the threshold detector be arranged, i.e., the reference voltage be selected, such that the detector detects a particular point during ventricular contraction.

It will be noted skilled persons may conclude that initiating inspiration during certain phases may cause air to be trapped in the lungs. However, it has been found that by utilizing the present invention one can balance trapped air and augmented blood flow. In other words, the benefit obtained by augmenting blood flow can be made greater than the detriment of having a small amount of air trapped in the lungs. Such a balancing is achieved by monitoring flow rate and pressure. The trapping of too great a volume of air in the lungs will result in significant increases in pressure. By utilizing the present invention to vary the provision of the control signal to the respirator, pressure can be maintained at acceptable levels, thus minimizing the amount of air trapped in the lungs.

In the preferred embodiment, the respirator is programmable so as to allow for adjustment of total volume, ECG phase delay, peak airway pressure, expiratory time, expiratory negative pressure assist as examples. In this regard, the cardiac gated ventilation can be tailored for patients with respiratory failure, rib cage abnormalities, variable lung compliance, etc. Programmed for high frequency ventilation, it may be desirable to superimpose inspiration pulses during the ventilation of the lungs. In such a situation, the enabling signal generated by controller 16 would be utilized to initiate such pulses in respirator. Consequently, the present invention is particularly useful as a method for treating coextensive respiratory and cardiac failure.

It will be noted that while the present invention is useful for treating coextensive failure, i.e. an extremely failing heart, the present invention is also useful in augmenting blood flow in a normal heart. In other words, the present invention can be used to augment blood flow in a case of respiratory failure.

While the invention has been described and illustrated with reference to specific embodiments, those skilled in the art will recognize that modification and variations may be made without departing from the principles of the invention as described herein above and set forth in the following claims.

What is claimed is:

1. Apparatus for maximizing the volume of blood pumped by a heart, wherein the lungs associated with said heart are ventilated by a respirator, wherein said respirator causes ventilation of said lungs in response to a control signal, said apparatus comprising:
    a first monitor for generating a heart signal representative of the action of said heart;
    a second monitor for generating a flow rate signal representative of the rate of flow of air into and out of said lungs;
    a third monitor for generating a pressure signal representative of the air pressure in said lungs; and
    a controller, connected to receive said heart signal, said flow rate signal, said pressure signal and to said respirator, for generating said control signal in response to said heart signal, said flow rate signal and said pressure signal, whereby blood being pumped from the heart is assisted by the ventilation of said lungs.

2. The apparatus of claim wherein said controller comprises a plurality of threshold detectors for detecting when said heart signal, said flow rate signal and said pressure signal exceed threshold levels.

3. The apparatus of claim 2, wherein said first monitor comprises an electro cardiogram signal generator, whereby said heart signal comprises an electrocardiogram signal.

4. The apparatus of claim 2, wherein said heart comprises a Ventricle and wherein said electrocardiogram signal is representative of the contraction of said ventricle, said threshold level representative of a point during said ventricular contraction, so that said detector detects a particular point during ventricular contraction.

5. The apparatus of claim 4, wherein each of said detectors comprises a comparator and a variable reference signal generator, whereby the comparator compares a monitor generated signal to a signal generated by the associated variable reference signal generator.

6. The apparatus of claim 1, wherein said controller comprises delay means for delaying the provision of said control signal to said respirator.

7. The apparatus of claim 6, wherein said delay means is operative in response to said flow rate signal and said pressure signal.

8. A system for maximizing the volume of blood pumped by a heart or optimizing ventilation/perfusion matching in the lungs, said system comprising:
    a programmable respirator for ventilating lungs associated with said heart, wherein said respirator causes inspiration in response to a control signal,
    a monitor for generating a heart signal representative of the action of said heart; and
    a controller, connected to receive said heart signal and to said respirator, for monitoring said heart signal and for generating said control signal when said heart signal is representative of the diastolic phase of said heart, whereby blood being pumped from the heart is assisted by the inspiration pulses generated by said ventilator.

9. A method for maximizing the volume of blood pumped by the heart of a patient or optimizing ventilation/perfusion matching in the lungs of a patient, said method comprising the steps of:
    ventilating said patient, wherein said ventilation is achieved in response to a control signal;
    generating a heart signal representative of the action of said heart;
    generating a flow rate signal representative of the flow rate of air into and out of said lungs;
    generating a pressure signal representative of the air pressure in said lungs; and
    generating said control signal in response to said heart signal, said flow rate signal and said pressure signal, whereby the pumping action of said heart is assisted by the ventilation of said lungs.

10. The method of claim 9, wherein said step of generating a control signal comprises the steps of monitoring said heart signal, said flow rate signal and said pressure signal and detecting when such signals exceed threshold levels.

11. The method of claim 10, wherein said step of generating a heart signal comprises the step of generating an electrocardiogram signal, whereby said heart signal comprises an electrocardiogram signal.

12. The method of claim 11, wherein said heart comprises a ventricle and wherein said step of generating an electrocardiogram signal comprises the step of generating a signal representative of the contraction of said ventricle, said threshold level representative of a point during said ventricular contraction, so that said step of monitoring comprises the step of detecting a particular point during ventricular contraction.

13. The method of claim 12, wherein said step of detecting a particular point during ventricular contraction comprises the steps of generating a variable reference signal and comparing said electrocardiogram signal to said variable reference signal.

14. The method of claim 10, further comprising the step of delaying said control signal.

15. The method of claim 14, wherein the step of delaying said control signal comprises the step of delaying said control signal until said heart is in the diastolic portion of its cycle.

16. A method for treating respiratory, cardiac or coextensive respiratory and cardiac failure, wherein heart and lungs are functioning abnormally, said method comprising the steps of:
    providing a respirator for ventilating said lungs, wherein said respirator is operative in response to a control signal;
    generating a heart signal representative of the action of said heart;
    generating a flow rate signal representative of the flow rate of air into and out of said lungs;
    generating a pressure signal representative of the air pressure in said lungs; and
    generating said control signal in response to said heart signal, said flow rate signal and said pressure signal, whereby the pumping action of said heart is assisted by the ventilation of said lungs.

* * * * *

UNITED STATES PATENT AND TRADEMARK OFFICE
CERTIFICATE OF CORRECTION

PATENT NO. : 5,188,098
DATED : February 23, 1993
INVENTOR(S) : Hoffman et al.

It is certified that error appears in the above-identified patent and that said Letters Patent is hereby corrected as shown below:

Column 3, Line 62 - after "source" a "V." should be typed.

Column 4, Line 14 - "1B" should be typed as "18".

Column 5, Line 52 - "if valve 34 is closed and valve 36 is" should be typed as "if valve 36 is closed and valve 34 is".

Column 6, Line 24 - "wi-11" should be typed as "will".

Column 7, Line 33 - after "claim" a "1" should be typed.

Signed and Sealed this

Twenty-third Day of November, 1993

*Attest:*

BRUCE LEHMAN

*Attesting Officer*    *Commissioner of Patents and Trademarks*